United States Patent [19]

Aldrich et al.

[11] 4,009,847

[45] Mar. 1, 1977

[54] 1-TERTIARY-ALKYL-3-(SUBSTITUTED THIENYL)UREAS AND 1-TERTIARY-ALKYL-3-(SUBSTITUTED THIETYL)UREAS AS ANTIHYPERTENSIVE AGENTS

[75] Inventors: Paul Edward Aldrich, Wilmington, Del.; Gilbert Harvey Berezin, West Chester, Pa.; Bruce Ivor Dittmar, Wilmington, Del.

[73] Assignee: E. I. Du Pont de Nemours and Company, Wilmington, Del.

[22] Filed: Mar. 11, 1975

[21] Appl. No.: 555,307

Related U.S. Application Data

[63] Continuation-in-part of Ser. No. 461,699, April 17, 1974, abandoned.

[52] U.S. Cl. .............................. 424/275; 260/332.1
[51] Int. Cl.² .......................................... A01N 9/00

[58] Field of Search ............. 424/275; 260/332.2 R, 260/332.1

[56] References Cited

UNITED STATES PATENTS 3,489,773   1/1970   Neeff et al. ..................... 260/332.1

*Primary Examiner*—James O. Thomas, Jr.
*Assistant Examiner*—A. Siegel

[57] ABSTRACT

This invention relates to a class of 1-tertiary-alkyl-3-(substituted thienyl)ureas and 1-tertiary-alkyl-3-(substituted thietyl)ureas that exhibit antihypertensive activity in warm-blooded animals. Representative compounds are 1-tert-butyl-3-(4,5-dihydro-3-thienyl)urea S,S-dioxide and 1-tert-butyl-3-(3-thiethyl)urea S,S-dioxide.

15 Claims, No Drawings

1-TERTIARY-ALKYL-3-(SUBSTITUTED THIENYL)UREAS AND 1-TERTIARY-ALKYL-3-(SUBSTITUTED THIETYL)UREAS AS ANTIHYPERTENSIVE AGENTS

CROSS-REFERENCE TO RELATED APPLICATION

This application is a continuation-in-part of my co-pending application Ser. No. 461,699, filed Apr. 17, 1974 now abandoned.

BACKGROUND OF THE INVENTION

It is well known that certain guanidine derivatives of tert-carbinamines possess antihypertensive (hypotensive) activity. Specific examples are tert-alkyl cyanoguanidines such as 1-tert-amyl-3-cyanoguanidine as described in S. M. Gadekar, S. Nibi, and E. Cohen, J. Med. Chem., 11, 811 (1968); and various derivatives of tert-alkyl guanidines such as tert-butyl guanidine, as described in J. H. Short, C. W. Ours, W. J. Ranus, Jr., J. Med. Chem., 11 1129 (1968).

However, urea derivatives are not represented in comprehensive discussions of antihypertensive agents. Such comprehensive discussions include W. T. Comer and A. W. Gomoll, Medicinal Chemistry, Third Edition, A. Burger, Wiley-Interscience, New York, 1970, pp. 1019–1064; and Medicinal Chemistry, Volume 7, "Antihypertensive Agents", E. Schlittler, Academic Press, New York, 1967. The urea-derivative compounds of this invention provide effective treatment of hypertension, yet differ structurally and chemically over antihypertensive agents currently known.

SUMMARY OF THE INVENTION

This invention relates to (a) compounds represented by the formula

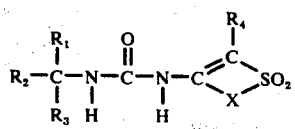

where $R_1$, $R_2$ and $R_3$ are $C_1$–$C_3$ alkyl or $C_2$–$C_3$ alkenyl, with the provisos that the total number of carbon atoms of $R_1$ plus $R_2$ plus $R_3$ does not exceed 5, and that two of $R_1$, $R_2$, and $R_3$ may be joined to form a cycloalkyl or cycloalkenyl group;

X is $-CH_2-$, $-CH_2-CH_2-$, or $-CHCH_2-$;
$\phantom{XXXXXXXXXXXXXXXXXXXXXXXXX}|$
$\phantom{XXXXXXXXXXXXXXXXXXXXXXXXX}CH_3$ $R_4$ is H or $CH_3$ with the proviso that when $R_4$ is $CH_3$, X is $-CH_2-$ or $-CH_2CH_2-$; and (b) sodium, potassium or calcium salts of compounds of (a), Preferred compounds within the scope of the above definition include those wherein $R_1$, $R_2$, and $R_3$ are $C_1$–$C_3$ alkyl.

Another embodiment of the invention relates to a method for treating hypertension in warm-blooded animals which comprises administering to said animal an antihypertensive amount of a compound of the invention.

Still another embodiment of the invention relates to pharmaceutical compositions which contain a compound of the invention in combination with suitable pharmaceutical adjuvants and modifiers.

DETAILED DESCRIPTION OF THE INVENTION

As indicated above, compounds of the invention include those of the formula

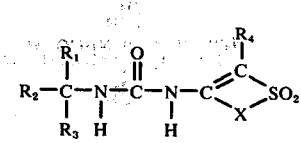

wherein $R_1$, $R_2$, $R_3$, $R_4$ and X are as previously defined. It is also to be understood that metal salts of the above-defined compounds are included within the scope of this invention. Illustrative of such metals are sodium, potassium and calcium. These salts are readily hydrolyzed to yield the respective free compounds.

The compounds of this invention are readily prepared as represented by the following equation:

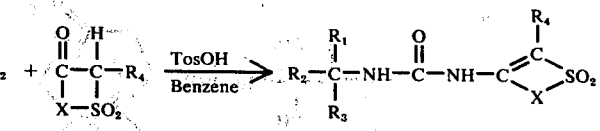

The compounds are prepared by heating equimolar amounts of the reactants in benzene with provision for water removal as, for example, a Dean-Stark water separator. In many cases water removal is not necessary. A catalytic amount of a strong acid (e.g., p-toluenesulfonic acid) is usually added to hasten the reaction. Although benzene is the preferred solvent, other solvents can be employed as, for example, toluene. Refluxing is continued until no more water is condensed in the Dean-Stark trap. Often the product precipitates during the course of the reaction and can subsequently be removed by filtration. Otherwise, it is isolated by chromatography and/or crystallization.

The salts of the compounds of this invention can be prepared by treating the compound with an alcoholic or aqueous solution of an equimolar amount of the respective alkali hydroxide and evaporating to dryness. In general, because the salts of these compounds hydrolyze readily, such salts are less desirable for use in formulating pharmaceutical compositions of the invention than the compounds per se.

The preparation of the compounds of this invention is illustrated but not limited by the following examples.

EXAMPLE 1

1-tert-butyl-3-(4,5-dihydro-3-thienyl)urea S,S-Dioxide

To a solution of 6.7 g 3-oxo-tetrahydrothiophene S,S-dioxide [(J. Chem. Soc. (C), 2171 (1967)] in 100 ml of benzene is added 5.6 g of tert-butyl urea and 100 mg p-toluene acid. The solution is heated at reflux under nitrogen with water removal for three hours. At the end of this period the solution is cooled and concentrated. The residual material is recrystallized from acetonitrile to give 6.8 g of 1-tert-butyl-3-(4,5-dihydro-3-thienyl)urea S,S-dioxide, m.p. 195°–197° C.

The infrared and n.m.r. spectra are consistent with the assigned structure.

EXAMPLES 2–12

Using the procedure described in Example 1, the reactants shown in column 1 produce the respective products of this invention as shown in column 2. In some cases it is preferable to purify the product using chromatography.

| Example | Reactants | Products |
|---|---|---|
| 2 | 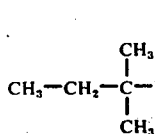 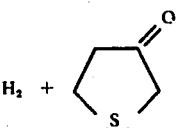 | 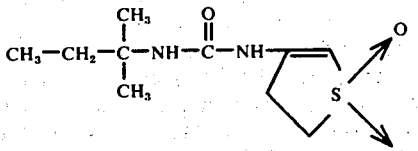<br>m.p. 184–186° C. |
| 3 | 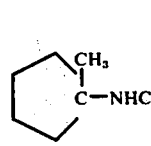 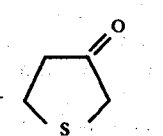 | 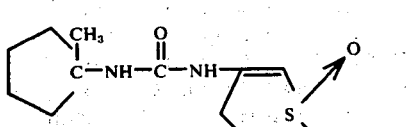<br>m.p. 210° C (dec) |
| 4 | 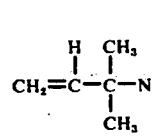 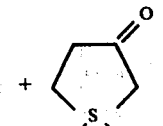 | 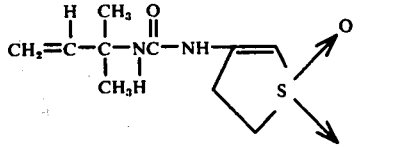<br>m.p. 172–174° C |
| 5 | 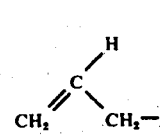 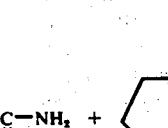 | 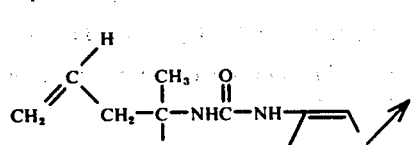 |
| 6 |  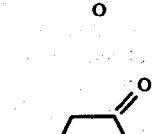 | 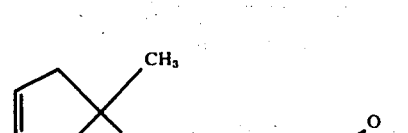 |
| 7 |   | 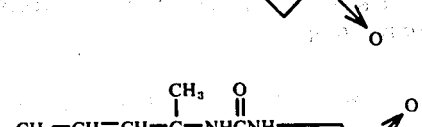 |

-continued

| Example | Reactants | Products |
|---|---|---|
| 8 | 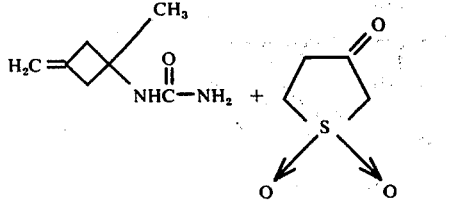 | 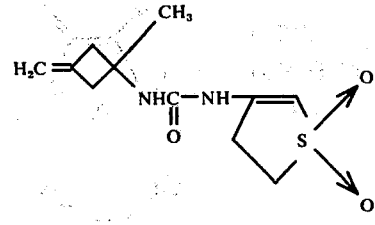 |
| 9 | 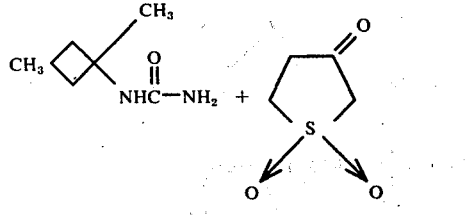 | 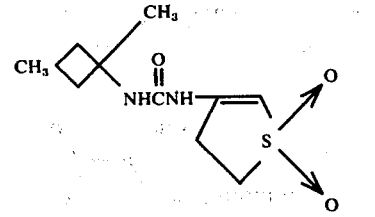 |
| 10 | 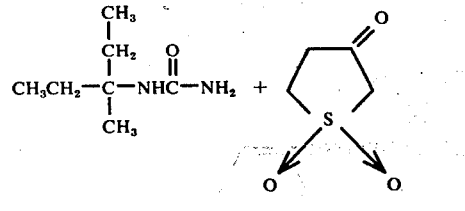 | 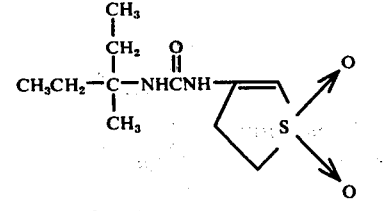 m.p. 197° C (dec.) |
| 11 | 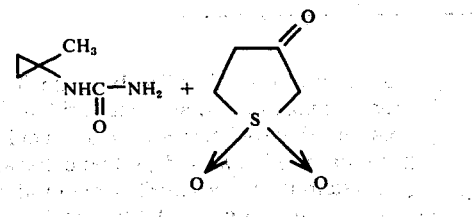 | 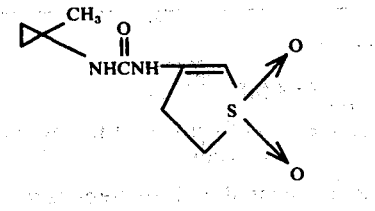 |
| 12 | 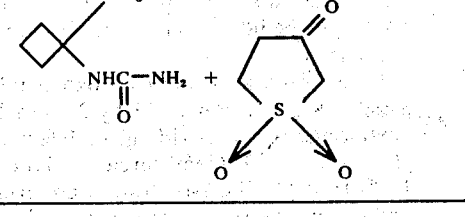 | 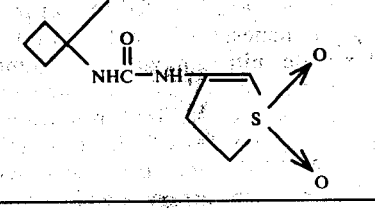 |

EXAMPLE 13

1-tert-butyl-3-(4-methyl-4,5-dihydro-3-thienyl)urea S,S-dioxide

To a solution of 6.4 g of 4-methyl-3-oxo-tetrahydrothiophene S,S-dioxide (E. Eigenberger, J. Prakt. Chem. 127, 307 (1930)) in 100 ml benzene is added 6.0 g of tert-butyl urea and 100 mg p-toluenesulfonic acid. The solution is heated at reflux under nitrogen with water removal using a Dean-Stark trap for 18 hours. At the end of this period the solution is cooled and concentrated. The residual material is chromatographed on 400 g of silicic acid using benzeneethyl acetate-methanol (6:3:1). The crystalline product obtained after chromatography is recrystallized from acetonitrile to give 4.5 g of 1-tert-butyl-3-(4-methyl-4,5-dihydro-3-thienyl)urea S,S-dioxide, m.p. 195° C dec. The structure is confirmed by infrared and n.m.r. spectra and elemental analysis.

EXAMPLES 14–17

Using the procedure described in Example 13, the reactants shown in column 1 produce the respective products of this invention as shown in column 2.

| Example | Reactants | Products |
|---|---|---|
| 14 | 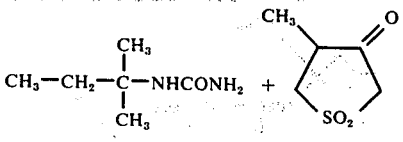 | 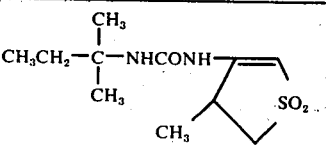<br>m.p. 178° C. (dec.) |
| 15 | 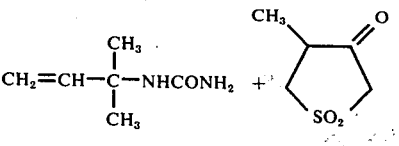 | 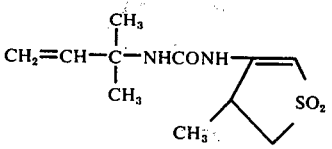<br>m.p. 174–176° C |
| 16 | 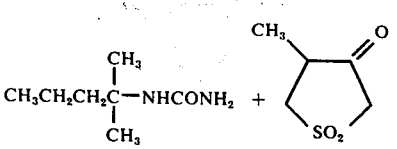 | 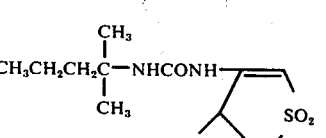<br>m.p. 122–124° C |
| 17 | 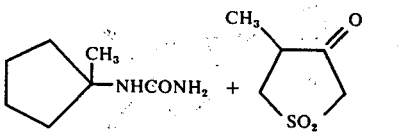 | 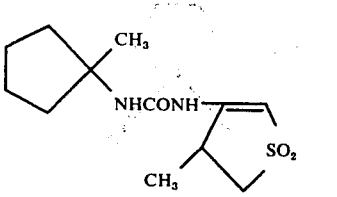<br>m.p. 167–169° C (dec.) |

EXAMPLE 18

1-tert amyl-3-(2-methyl-4,5-dihydro-3-thienyl)urea S,S-dioxide

This compound is prepared in three steps as follows:

1. To a solution of 18 g 3-oxo-tetrahydrothiopene S,S-dioxide in 150 ml benzene is added 15 g of pyrrolidine and 100 mg p-toluenesulfonic acid. The solution is heated at reflux under nitrogen with water removal for four hours. The solution is cooled and the gummy precipitate is filtered and recrystallized from acetonitrile to give 15 g of 3-pyrrolidino-4,5-dihydro-3-thiene S,S-dioxide, m.p. 148°–150° (decomp.). The structure is confirmed by infrared n.m.r. spectra and elemental analysis.

2. To a solution of 12 g of 3-pyrrolidine-4,5-dihydro-3-thiene S,S-dioxide in 50 ml dioxane is added 20 ml of methyl iodide. The solution is heated at reflux under nitrogen with stirring for 20 hours. At one end of this period 25 ml of water and 3 ml of acetic acid are added and one solution is heated at reflux for six hours. At the end of this period, the solution is cooled and concentrated. The residual material is extracted with three 150 ml portions of boiling benzene. The benzene solution is concentrated and one residual material is chromatographed on 100 g of silicic acid. Elution with a solution of ethyl acetate, toluene, hexane (6:3:1) gives a crystalline material. This material is recrystallized from ethanol to give 2-methyl-3-oxotetrahydrothiophene S,S-dioxide, m.p. 83°–85° C. The structure is confirmed by infrared and n.m.r. spectra and elemental analysis.

3. Replacing 4-methyl-3-oxo-tetrahydrothiophene S,S-dioxide in Example 13 by 2-methyl-3-oxo-tetrahydrothiophene S,S-dioxide gives 1-tert amyl-3-(2-methyl-4,5-dihydro-3-thienyl)urea S,S-dioxide, m.p. 160°–162° C. The structure is confirmed by infrared and n.m.r. spectra an elemental analysis.

EXAMPLE 19

1-tert amyl-3-(5-methyl-4,5-dihydro-3-thienyl)urea S,S-dioxide

5-Methyl-3-oxo-tetrahydrothiophene S,S-dioxide, one of the starting materials for synthesis of 1-tert amyl-3-(5-methyl-4,5-dihydro-3-thienyl)urea S,S-dioxide, is prepared as follows:

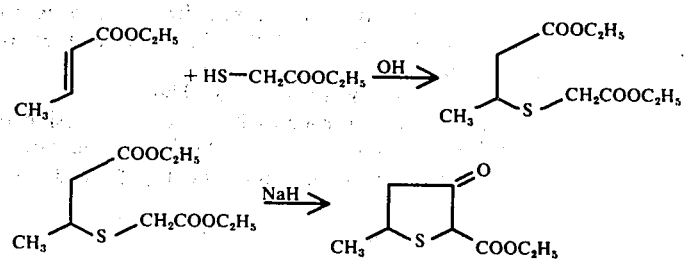

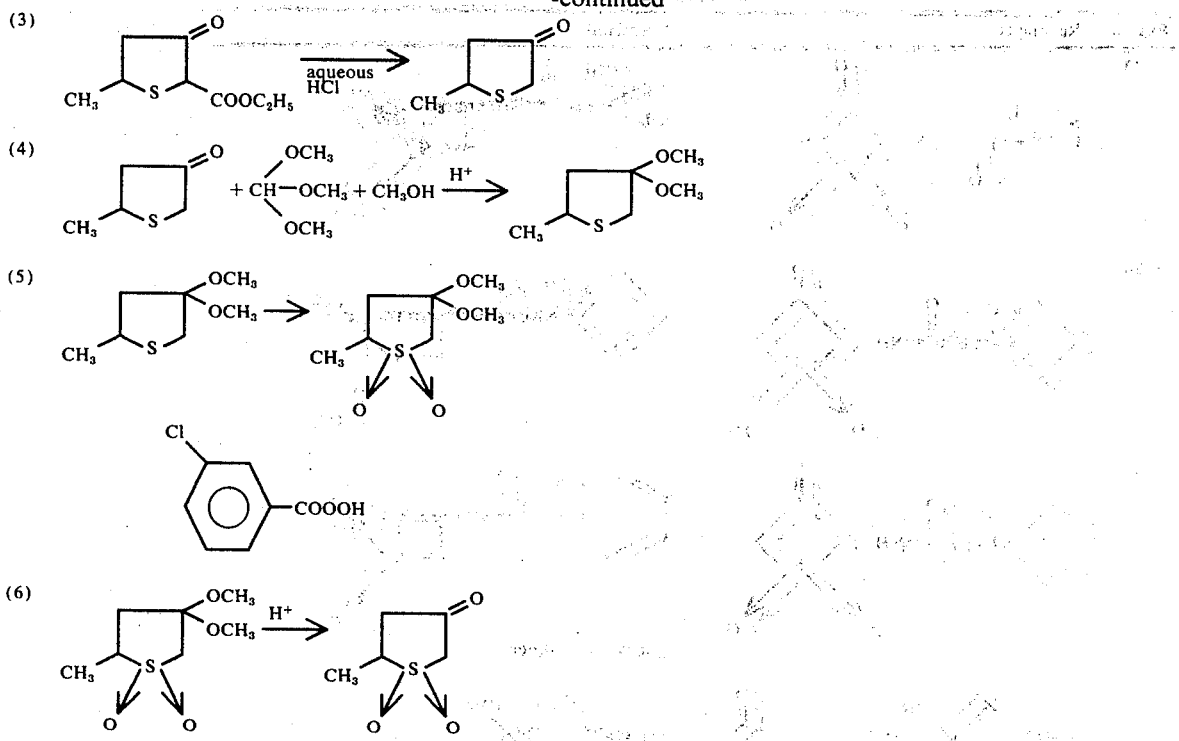

The procedure of Example 13 is used except that 4-methyl-3-oxo-tetrahydrothiophene S,S-dioxide is replaced with 5-methyl-3-oxo-tetrahydrothiophene S,S-dioxide to give 1-tert-amyl-3-(5-methyl-4,5-dihydro-3-thienyl)urea S,S,-dioxide.

EXAMPLES 20–28

Using the procedure described in Example 13, the reactants shown in column 1 produce the respective products of this invention as shown in column 2. The 3-thietanone S,S-dioxide starting material is prepared as described by Truce and Campbell, J. Am. Chem. Soc. 88, 3599 (1966).

| Example | Reactants | Products |
|---|---|---|
| 20 | 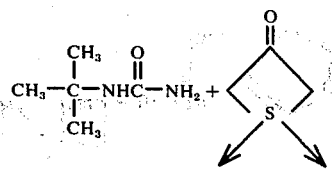 | 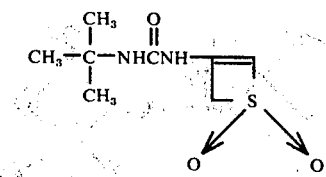 m.p. 180–181° C (dec.) |
| 21 | 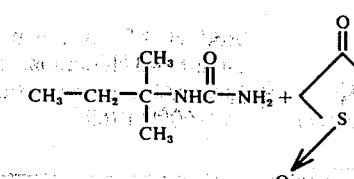 | 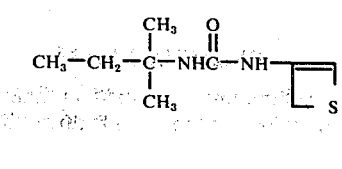 m.p. 180° C (dec.) |
| 22 | 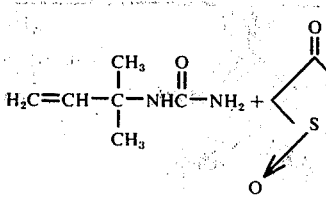 | 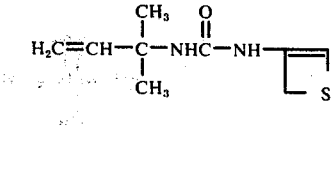 |

-continued

| Example | Reactants | Products |
|---|---|---|
| 23 | (1-methylcyclopropyl)NHC(O)NH₂ + 3-oxothietane-1,1-dioxide | (1-methylcyclopropyl)NHC(O)NH-(thietane S,S-dioxide) |
| 24 | (1-methylcyclobutyl)NHC(O)NH₂ + 3-oxothietane-1,1-dioxide | (1-methylcyclobutyl)NHC(O)NH-(thietane S,S-dioxide) |
| 25 | (1-methylcyclopentyl)NHC(O)NH₂ + 3-oxothietane-1,1-dioxide | (1-methylcyclopentyl)NHC(O)NH-(thietane S,S-dioxide)  m.p. 182° C (dec.) |
| 26 | (3-methylene-1-methylcyclobutyl)NHC(O)NH₂ + 3-oxothietane-1,1-dioxide | (3-methylene-1-methylcyclobutyl)N=C(OH)NH-(thietane S,S-dioxide) |
| 27 | (3-methyl-1-methylcyclobutyl)NHC(O)NH₂ + 3-oxothietane-1,1-dioxide | (3-methyl-1-methylcyclobutyl)NHC(O)NH-(thietane S,S-dioxide) |
| 28 | (1-methyl-3-cyclohexenyl)NHC(O)NH₂ + 3-oxothietane-1,1-dioxide | (1-methyl-3-cyclohexenyl)NHC(O)NH-(thietane S,S-dioxide) |

EXAMPLES 29–33

Using the procedure described in Example 13, the reactants shown in column I produce the respective products of this invention as shown in column II. The 2-methyl-3-thietanone S,S-dioxide starting material is prepared as described by M. H. Rosen, Tet. Letters 8, 647–650 (1969).

| Examples | I Reactants | II Product |
|---|---|---|
| 29 | (CH₃)₃C-NH-C(O)-NH₂ + 2-methyl-3-oxothietane-1,1-dioxide | (CH₃)₃C-NHC(O)-NH-(2-methyl thietane S,S-dioxide) |

-continued

| Examples | I Reactants | II Product |
|---|---|---|
| 30 | CH₃—CH₂—C(CH₃)(—NHC(O)—NH₂) + [2-methyl-tetrahydrothiophene-3-one S,S-dioxide] | CH₃—CH₂—C(CH₃)₂—NHC(O)—NH—[4-methyl-4,5-dihydro-3-thienyl] S,S-dioxide; dimorphic: m.p. 120–122° and m.p. 140–141° C |
| 31 | CH₃—CH₂—C(CH₃)(CH₂C(O)NHCNH₂) + [2-methyl-tetrahydrothiophene-3-one S,S-dioxide] | CH₃—CH₂CH₂—C(CH₃)(O)—NHCNH—[4-methyl-4,5-dihydro-3-thienyl]; m.p. 153–154° C |
| 32 | H₂C=C(H)—C(CH₃)(CH₃)—NHC(O)—NH₂ + [2-methyl-tetrahydrothiophene-3-one S,S-dioxide] | H₂C=C(CH₃)—C(CH₃)(—N(H)—C(O)—NH—[4-methyl-4,5-dihydro-3-thienyl] S,S-dioxide) |
| 33 | 1-methylcyclopentyl-NHC(O)NH₂ + [2-methyl-tetrahydrothiophene-3-one S,S-dioxide] | 1-methylcyclopentyl-NHC(O)—NH—[4-methyl-4,5-dihydro-3-thienyl] S,S-dioxide |

The compounds of this invention can be administered in the treatment of hypertension according to the invention by any means that effects contact of the active ingredient compound with the site of action in the body of a warm-blooded animal. For example, administration can be parenteral, i.e., subcutaneous, intravenous, intramuscular, or intraperitoneal. Alternatively or concurrently, administration can be by the oral route.

For the purpose of this disclosure, a warm-blooded animal is a member of the animal kingdom possessed of a homostatic mechanism and includes mammals and birds.

The dosage administered will be dependent on the age, health, and weight of the receipient, the extent of disease, kind of concurrent treatment, if any, frequency of treatment, and the nature of the effect desired. Usually, a daily dosage of active ingredient compound will be from about 0.1 to 50 milligrams per kilogram of body weight. Ordinarily, from 0.5 to 40, and preferably, 1.0 to 20, milligrams per kilogram per day in one or more applications per day is effective to obtain desired results. For the more potent compounds of the invention, e.g., 1-tert-amyl-3-(4,5-dihydro-3-thienyl)urea S,S-dioxide, the daily dosage ranges are from about 0.1 to 20 mg/kg, preferably 0.5 to 15 mk/kg, and more preferably 1.0 to 10 mg/kg.

The antihypertensive activity of the compounds of this invention is evidenced by tests conducted in hypertensive rats and by further tests which show a blood pressure lowering effect in normotensive dogs.

In these tests rats are made hypertensive by repeated injections of desoxycorticosterone acetate (DOCA) and by giving the rats saline solution to drink essentially according to the method described by Stanton and White [Arch. Intern. Pharmacodyn., 154, 351 (1965)]. Graded dose levels of each compound are administered orally to groups of eight hypertensive rats. The compound is prepared in a aqueous polyvinyl alcohol-/acacia vehicle and administered at a volume to body weight ratio of 5.0 ml/kg. Sixteen hypertensive rats receiving the aqueous vehicle by the same route serve as controls for each test. At various intervals of time after treatment, usually 90 minutes, the systolic arterial blood pressure of each rat is determined by a modification of the microphone-manometer technique [Friedman, M. and Freed, S. C., Proc. Soc. Exp. Biol. and Med., 70, 670 (1969)]. That dose of compound which produces a 30 mm mercury (mm Hg) reduction in blood pressure when compared to the mean systolic arterial blood pressure of the control animals is then determined (Effective Dose 30). For example, an ED30 of 6.0 mg/kg orally was obtained with 1-tert-amyl-3-(4,5-dihydro-3-thienyl)urea, S,S-dioxide. An $ED_{30}$ of 12.0 was obtained with 1-tert-butyl-3-(4,5-dihydro-3-thienyl)urea S,S-dioxide. An $ED_{30}$ of 1.7 was obtained with 1-tert-amyl (4-methyl-4,5-dihydro-3-thienyl) urea S,S-dioxide.

In a test involving dogs, these compounds are administered intravenously (i.v.) to eight anesthetized normotensive dogs according to a cumulative dose schedule. Arterial blood pressure is recorded directly through an arterial cannula and a polygraph by which it is determined that the compound shows statistically significant blood pressure lowering in comparison to the predosing control value and to the effect of vehicle on control animals.

The compounds of this invention can be employed in useful pharmaceutical compositions according to the present invention in such dosage forms as tablets, capsules, powder packets, or liquid solutions, suspensions or elixirs for oral administration or liquid for parenteral use, and in certain cases, suspensions for parenteral use (except intravenous injections). In such compositions, the active ingredient will ordinarily always be present in an amount of at least 0.5% by weight based on the total weight of the composition and not more than 95% by weight.

Besides the active ingredient compounds of this invention, the antihypertensive composition will contain a solid or liquid non-toxic pharmaceutical carrier for the active ingredient.

In one embodiment of a pharmaceutical composition of this invention, the solid carrier is a capsule which can be of the ordinary gelatin type. In the capsules will be from about 5 to 90% by weight of a compound of the invention and 95 to 10% of a carrier. In another embodiment, the active ingredient is tableted with or without adjuvants. In yet another embodiment, the active ingredient is put into powder packets and employed. These capsules, tablets, and powders will generally constitute from about 1% to about 95% and preferably from 5% to 90% by weight of active ingredient. These dosage forms preferably contain from about 5 to 500 milligrams of active ingredient, with about 7 to about 250 most preferred.

The pharmaceutical carrier can, as previously indicated, be a sterile liquid such as water and oil, including those of petroleum, animal, vegetable oils of synthetic origin, for example peanut oil, soybean oil, mineral oil, sesame oil, and the like. In general, water saline, aqueous dextrose (glucose), and related sugar solutions and glycols such as propylene glycol or polyethylene glycols are preferred liquid carriers, particularly for injectible solutions. Sterile injectible solutions, such as saline, will ordinarily contain from about 0.5% to 25% and preferably about 1 to 10% by weight of the active ingredient.

As mentioned above, oral administration can be in a suitable suspension or syrup, in which the active ingredient ordinarily will constitute from about 0.7 to 10% and preferably about 1 to 5%, by weight. The pharmaceutical carrier in such composition can be a watery vehicle such as an aromatic water, a syrup, or a pharmaceutical mucilage.

Suitable pharmaceutical carriers are described in "Remington's Pharmaceutical Sciences" by E. W. Martin, a well-known reference text in this field.

The following examples will further illustrate the preparation of pharmaceutical compositions of the invention.

EXAMPLE A

A large number of unit capsules are prepared by filling standard two-piece hard gelatin capsules each with 250 milligrams of powdered 1-tert-butyl-3-(4,5-dihydro-3-thienyl)urea S,S-dioxide, 110 milligrams of lactose, 32 milligrams of talc, and 8 milligrams of magnesium stearate.

EXAMPLE B

A mixture of 1-tert-amyl-3-(4,5-dihydro-3-thienyl) urea S,S-dioxide in soybean oil is prepared and injected by means of a positive displacement pump into gelatin to form soft gelating capsules containing 35 milligrams of the active ingredient. The capsules are washed in petroleum ether and dried.

EXAMPLE C

A large number of tablets are prepared by conventional procedures so that the dosage unit is 100 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch, and 98.8 milligrams of lactose. Appropriate coatings may be applied to increase palatability or delay absorption.

EXAMPLE D

A parenteral composition suitable for administration by injection is prepared by stirring 1.5% by weight of 1-(1-methylcyclopentyl)-3-(4,5-dihydro-3-thienyl)urea S,S-dioxide in 10% by volume propylene glycol and water. The solution is sterilized by filtration.

EXAMPLE E

An aqueous suspension is prepared for oral administration so that each 5 milliliters contain 50 milligrams of finely divided 1-tert-butyl-3-(4,5-dihydro-3-thienyl-)urea S,S-dioxide, 500 milligrams of acacia, 5 milligrams of sodium benzoate, 1.0 grams of sorbitol solution, U.S.P., 5 milligrams of sodium saccharin, and 0.025 milliliters of vanilla tincture.

EXAMPLE F

A parenteral composition suitable for administration by injection is prepared by dissolving 1% by weight of 1-tert-amyl-3-(4,5-dihydro-3-thienyl)urea. S,S-dioxide in sodium chloride injection U.S.P. XV and adjusting the pH of the solution to between 6 and 7. The solution is sterilized by filtration.

A wide variety of compositions coming within this invention can be prepared by substituting other compounds of this invention, including specifically but not limited to those compounds named hereinbefore, for the compounds named in Examples A–F above and substituting other suitable pharmaceutical carriers well known and described in the Martin text mentioned above.

What is claimed is:

1. A compound of the formula:

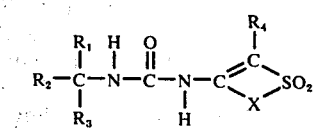

where
$R_1$, $R_2$ and $R_3$ are $C_1$–$C_3$ alkyl, or $C_2$–$C_3$ alkenyl, with the provisos that the total number of carbon atoms of $R_1$ plus $R_2$ plus $R_3$ does not exceed 5

X is $-CH_2CH_2-$ or $-\underset{\underset{CH_3}{|}}{CH}-CH_2-$;

$R_4$ is H or $CH_3$ with the proviso that when $R_4$ is $CH_3$, X is $-CH_2CH_2-$; and its sodium, potassium, or calcium salts.

2. The compound of claim 1 wherein $R_1$, $R_2$, and $R_3$ are $C_1-C_3$ alkyl.

3. The compound of claim 2 which is 1-tert-butyl-3-(4,5-dihydro-3-thienyl)urea S,S-dioxide.

4. The compound of claim 2 which is 1-tert-amyl-3-(4,5-dihydro-3-thienyl)urea S,S-dioxide.

5. The compound of claim 2 which is 1-tert-amyl-3-(4-methyl-4,5-dihydro-3-thienyl)urea S,S-dioxide.

6. A method of treating hypertension in a warm-blooded animal comprising administering to the warm-blooded animal an effective antihypertensive amount of a compound of claim 1.

7. A method of treating hypertension in a warm-blooded animal comprising administering to the warm-blooded animal an effective antihypertensive amount of a compound of claim 2.

8. A method of treating the hypertension in a warm-blooded animal comprising administering to the warm-blooded animal an effective antihypertensive amount of a compound of claim 3.

9. A method of treating hypertension in a warm-blooded animal comprising administering to the warm-blooded animal an effective antihypertensive amount of a compound of claim 4.

10. A method of treating hypertension in a warm-blooded animal comprising administering to the warm-blooded animal an effective antihypertensive amount of a compound of claim 5.

11. A pharmaceutical composition comprising a suitable pharmaceutical carrier and an effective antihypertensive amount of a compound of claim 1.

12. A pharmaceutical composition comprising a suitable pharmaceutical carrier and an effective antihypertensive amount of a compound of claim 2.

13. A pharmaceutical composition comprising a suitable pharmaceutical carrier and an effective antihypertensive amount of a compound of claim 3.

14. A pharmaceutical composition comprising a suitable pharmaceutical carrier and an effective antihypertensive amount of a compound of claim 4.

15. A pharmaceutical composition comprising a suitable pharmaceutical carrier and an effective antihypertensive amount of a compound of claim 5.

* * * * *